US008226635B2

(12) United States Patent
Petrie et al.

(10) Patent No.: US 8,226,635 B2
(45) Date of Patent: Jul. 24, 2012

(54) DEVICE FOR CIRCULATING HEATED FLUID

(75) Inventors: Aidan Petrie, Jamestown, RI (US); Andrew W. Marsella, Boston, MA (US); Daniel Nelsen, Providence, RI (US); David Robson, Riverside, RI (US); Joseph M. Gordon, Mansfield, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1321 days.

(21) Appl. No.: 11/870,678

(22) Filed: Oct. 11, 2007

(65) Prior Publication Data
US 2008/0097563 A1 Apr. 24, 2008

Related U.S. Application Data

(60) Provisional application No. 60/853,659, filed on Oct. 23, 2006.

(51) Int. Cl.
*A61B 18/04* (2006.01)

(52) U.S. Cl. .................. 606/27; 606/28; 606/29

(58) Field of Classification Search ............. 600/29; 607/104–106, 113; 395/61; 606/27–29
See application file for complete search history.

(56) References Cited

U.S. PATENT DOCUMENTS

| 5,746,719 | A  | * | 5/1998  | Farra et al. ............. 604/151 |
| 5,891,094 | A  | * | 4/1999  | Masterson et al. ....... 604/113 |
| 7,563,248 | B2 | * | 7/2009  | Smisson et al. .......... 604/122 |
| 2003/0204185 | A1 |   | 10/2003 | Sherman et al. |
| 2007/0066929 | A1 | * | 3/2007  | Ferren et al. ............... 604/8 |

FOREIGN PATENT DOCUMENTS

| WO | 94/17842 | 8/1994 |
| WO | 98/57603 | 12/1998 |
| WO | 99/60960 | 12/1999 |
| WO | 01/64120 | 9/2001 |
| WO | 02/17805 | 3/2002 |
| WO | 2006/044581 | 4/2006 |

* cited by examiner

*Primary Examiner* — Roy Gibson
(74) *Attorney, Agent, or Firm* — Fay Kaplun & Marcin, LLP

(57) ABSTRACT

A system for ablating tissue includes a reusable control unit including a processor monitoring and controlling ablation and a control interface receiving input to and output from the processor in combination with a disposable procedure set releasably connectable to the control unit to couple to the control interface for communication with the processor.

25 Claims, 12 Drawing Sheets

System Block Diagram

System Block Diagram

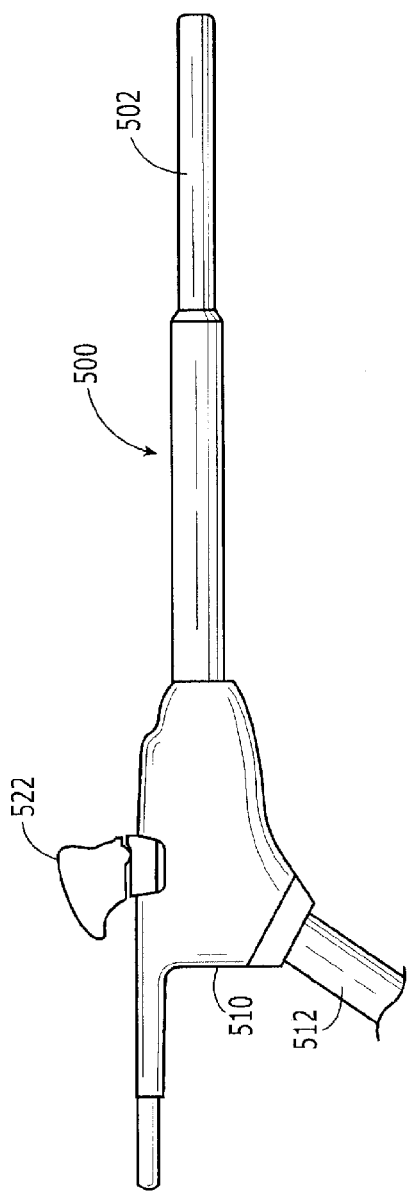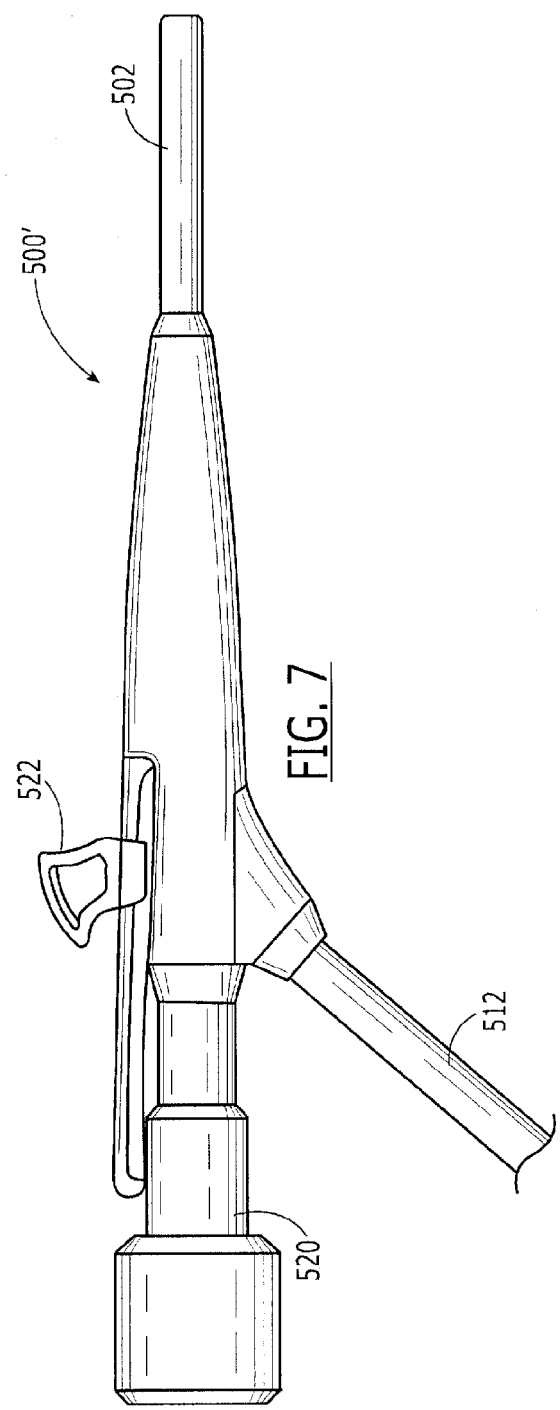

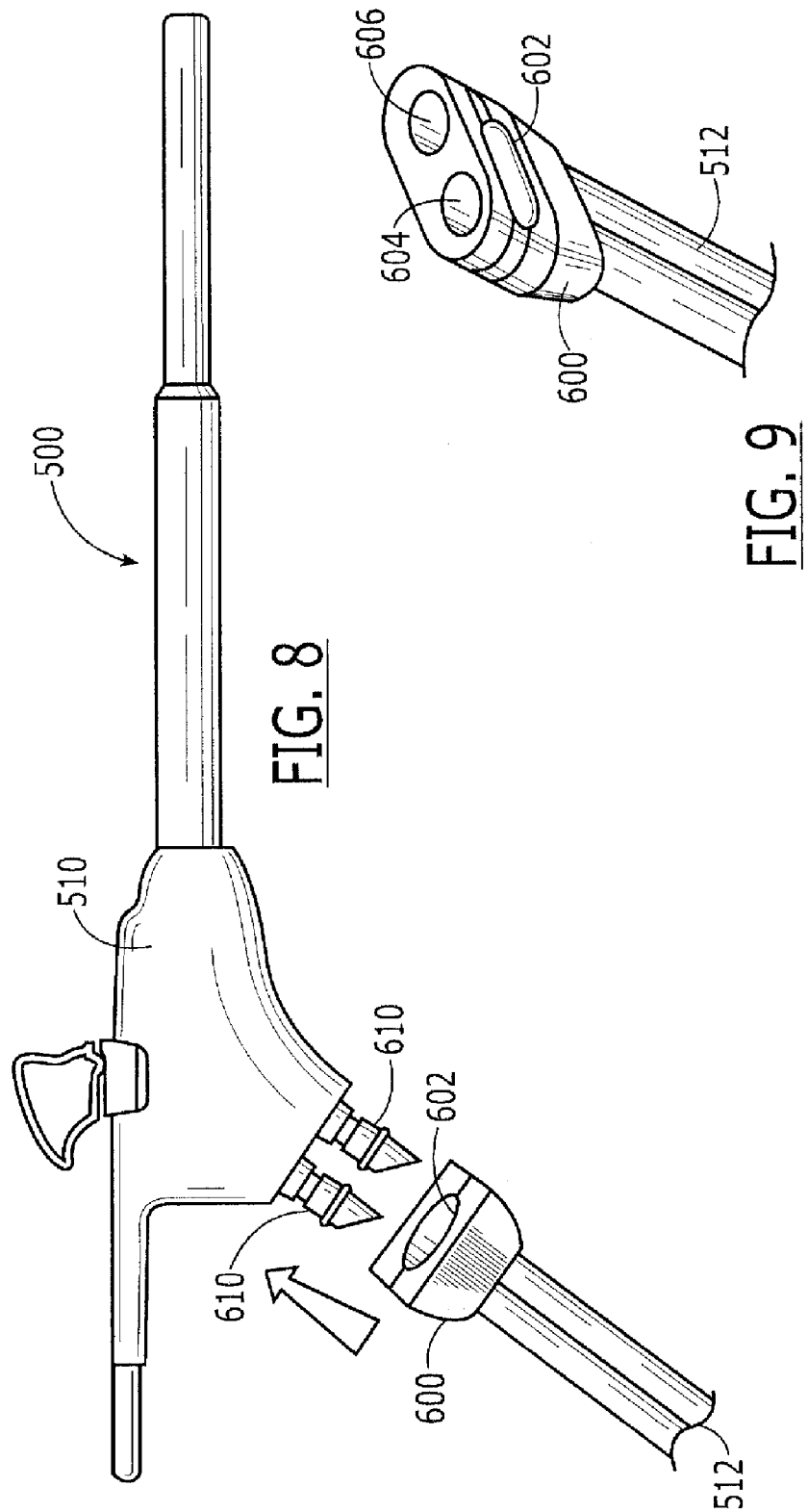

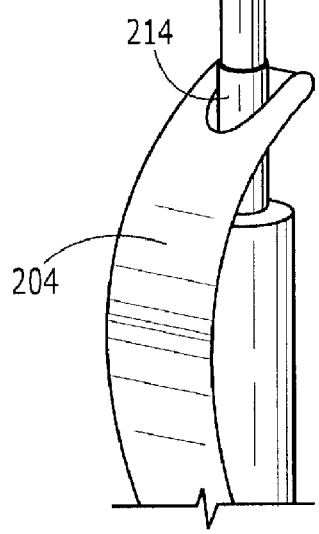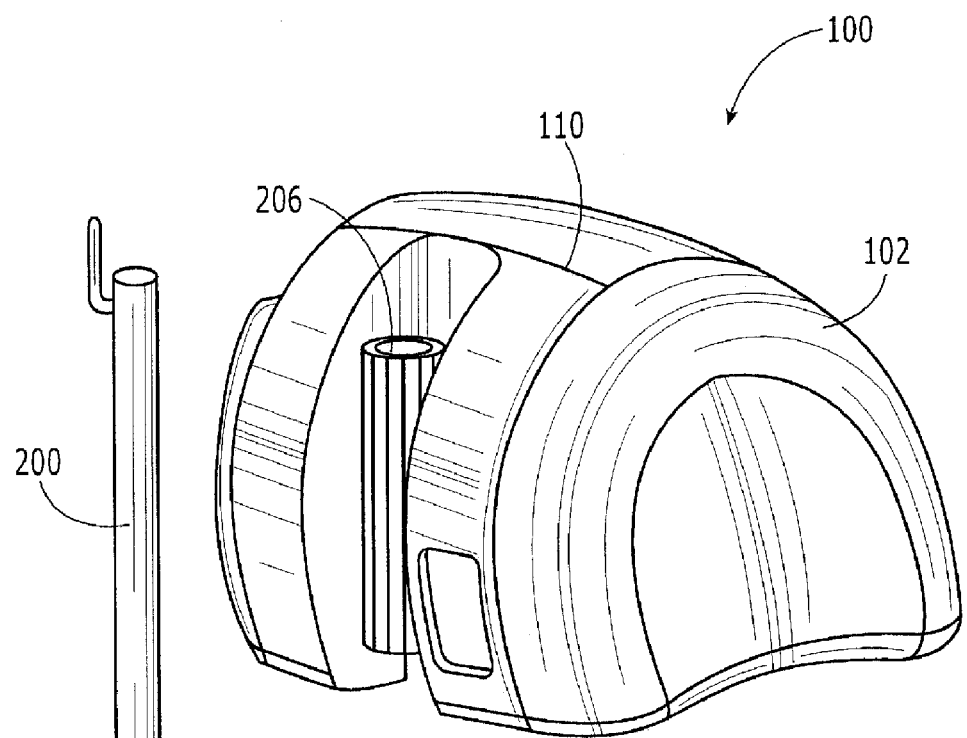
FIG. 10

US 8,226,635 B2

DEVICE FOR CIRCULATING HEATED FLUID

PRIORITY CLAIM

This application claims the priority to the U.S. Provisional Application Ser. No. 60/853,659, entitled "Device for Circulating Heated Fluid," filed Oct. 23, 2006. The specification of the above-identified application is incorporated herewith by reference.

BACKGROUND INFORMATION

Excessive or dysfunctional uterine bleeding often arises from a hormonal imbalance, a systemic disease or anatomical abnormality such as fibroids, polyps or other growths. Invasive surgical treatments such as hysterectomies as well as significantly less drastic procedures are complex and expensive and often involve significant discomfort and complications. Furthermore, available non-surgical procedures including medication and hormone therapies are often insufficient.

A common, less invasive alternative is ablation of the lining of the uterus. In hydro-thermal ablation (HTA), heated saline solution is applied against targeted portions of the endometrial lining through a hysteroscope inserted through the cervix. The endometrial lining may also be ablated by applying a cryogenic fluid, electromagnetic energy or a chemically ablative agent.

The users of conventional ablation devices must monitor pressure and temperature of the saline and the status of surgical tools used, increasing the complexity and cost of the procedures. Furthermore, these devices are not well designed for interaction with related components and may be difficult to integrate into a procedure as a whole.

SUMMARY OF INVENTION

The present invention relates to a system for ablating tissue. The system includes a reusable control unit which includes a processor monitoring and controlling ablation and a control interface receiving input to and output from the processor. The system also includes a disposable procedure set releasably connectable to the control unit to couple to the same control interface for communication with the processor.

The present invention also relates to a control system for an hydro-thermal ablation procedure. The control system also relates to a reusable console including a processor monitoring and controlling the hydro-thermal ablation procedure and a disposable cartridge selectively coupleable to the console, the cartridge including a plurality of sensors connectable to the processor. The sensors measure properties of an ablation fluid. A mechanical safety interlock of the processor inhibits the hydro-thermal ablation procedure when commanded by the processor. The control system further includes an ablation fluid control system including a pump and a heater controlled by the processor.

BRIEF DESCRIPTION OF THE DRAWINGS

FIG. 6 is a representation of a first embodiment of the ergonomic handle used in the system according to the present invention;

FIG. 7 is a representation of a second embodiment of the ergonomic handle used in the system according to the present invention;

FIG. 8 is a representation of an embodiment of an ergonomic handle used in the system with a quick disconnect fitting, according to the present invention;

FIG. 9 is a detail representation of the female portion of the quick disconnect fitting of FIG. 8, according to the present invention;

FIG. 10 is a perspective view of a pole mount fixture and console unit according to an embodiment of the present invention;

DETAILED DESCRIPTION

Figure 1:
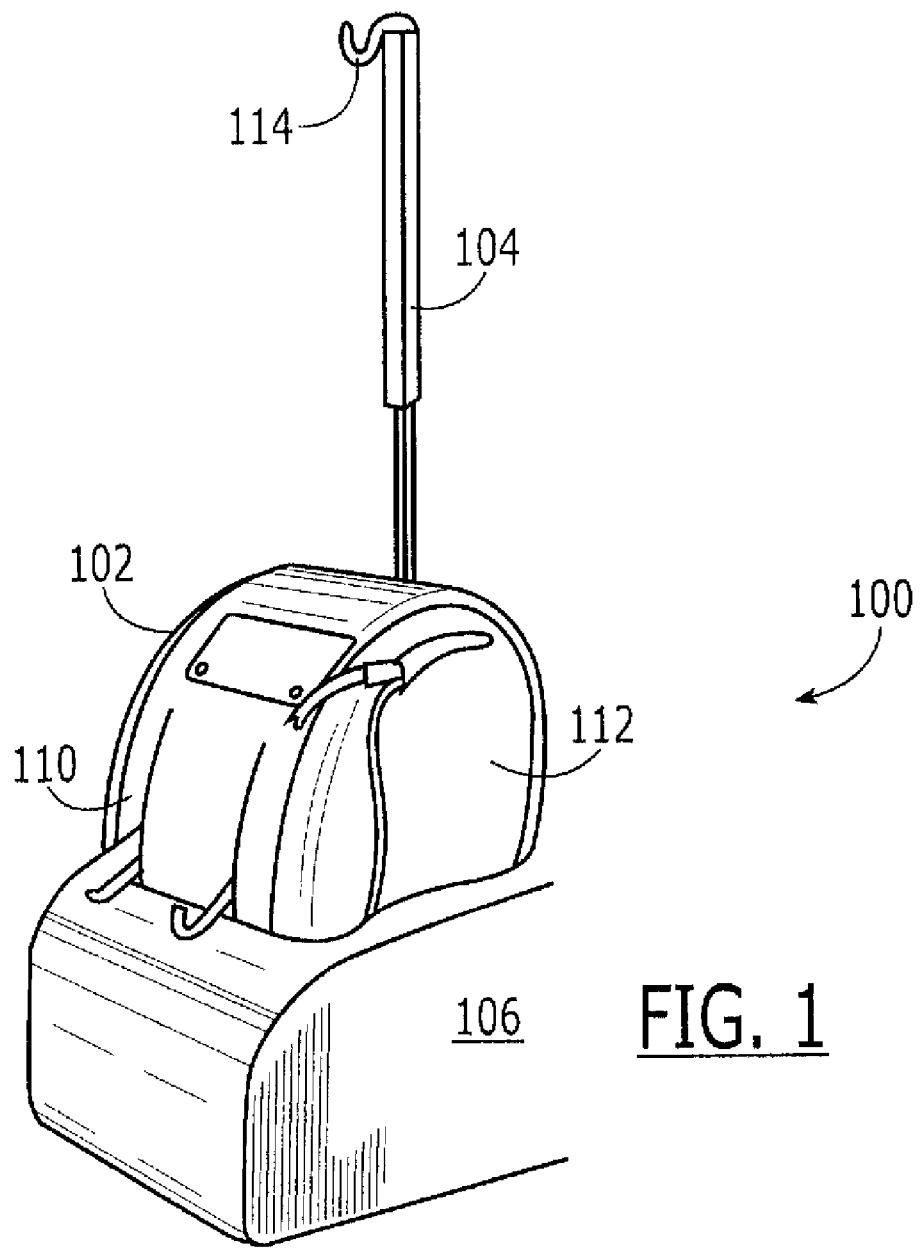
FIG. 1 is a perspective view showing an embodiment of a console unit of a device for circulating heated fluid to a patient according to the invention.

The present invention may be further understood with reference to the following description and the appended drawings, wherein like elements are referred to with the same reference numerals. The present invention relates to devices for treating the uterus and, more particularly, relates to software controlled devices for treating the lining of the uterus using a fluid at a controlled pressure and temperature.

As described above, endometrial ablation procedures are often carried out by inserting surgical tools into the uterus through the vagina and the cervix with no incision through the abdomen. In some cases, a hysteroscope is used to facilitate the insertion of tools through the cervix to the operative area. Depending on the procedure, these medical tools may include devices to monitor the procedure, to position and/or activate one or more electrodes or cryogenic elements, conduits for heated and/or high pressure fluids, etc.

The present invention is related to a software controlled hydro-thermal ablation system including components designed to work together as an integrated whole. The system according to the present invention monitors various parameters and presents data to the user to enhance the monitoring and control of the thermal ablation treatment.

In one exemplary embodiment, the hydro-thermal ablation system according to the invention comprises a console carrying out control functions for the system and a disposable, sterile procedure set which handles fluids sent to and received from the patient. As the console unit does not contact fluids reaching the patient, it is reusable without the need for sterilization. Only the procedure set is disposed of after each use, reducing the overall cost of the treatment. Although described in regard to a system for hydro-thermal ablation of the endometrium, those skilled in the art will understand that the system according to the invention can be used in a variety of procedures for ablating tissue within a variety of hollow organs.

As indicated above, the exemplary hydro-thermal ablation system comprises a console including hardware components, software elements and interface features for powering and controlling various functions of the device in combination with the sterile procedure set. For example, pumping, heating and sensing during the ablation procedure may be controlled as necessary by the console to maintain the parameters of the procedure within ranges designed to ensure the procedure is effective and safe. In one exemplary embodiment of a system according to the invention, the console monitors and controls other components of the system to accurately deliver to a patient a 0.9% saline solution heated to approximately 90° C. at a pressure of approximately 50±5 mmHg and a flow rate of about 200-300 ml/min.

The hardware and software of the console also monitor multiple parameters relating to the procedure including, for example, changes in fluid level, the formation of clogs in fluid passages of the system, etc. As would be understood by those skilled in the art, the system may monitor any parameters related to conditions impacting patient safety and/or the effectiveness of the treatment including, for example, overpressurization of the uterine cavity, absorption of the ablation fluid and/or a reduced flow of fluid. The electronic monitoring provided by elements of the console may also recognize the status of disposable components of the system to ensure that they are suitable for the current procedure (e.g., to ensure that single use elements have not previously been used, that they are operating effectively and safely, etc.).

FIG. 1 shows an exemplary embodiment of a console according to the hydro-thermal ablation system of the invention. The hydro-thermal ablation system 100 may be used in two different modes. In the configuration shown in FIG. 1, the hydro-thermal ablation system 100 comprises a table top or cart top mounted unit 102 designed to rest on a planar surface, such as the cart 106. The unit 102 comprises a console 110 as well as a disposable cartridge 112 including various elements of the disposable sterile procedure set. The console 110 is designed so that the user can place it on top of a table or rolling cart, as shown, during operation. However in this mode of operation, it may be necessary to install a short custom fluid pole 104 on the console 110, so that accessories can be suspended therefrom. For example, a bag containing saline solution may be suspended from a hook 114 of the pole 104.

In a second operating mode, the console 110 may be mounted to a standard full length IV fluid pole, of the type commonly found in surgical settings. In this operating mode, the hydro-thermal ablation system 100 is attached by a clamping arrangement that is integral with the console 110, as will be described in greater detail below. By providing both of these mounting options in one unit, the users can easily adapt the hydro-thermal ablation system 100 to various operating environments. Many conventional medical devices are designed to be either fixed on a pole, such as an IV fluid pole, or to be free standing on a table top or cart top surface. However, the ability to mount the console 110 in either mode gives the systems 100 according to the present invention additional flexibility. A handle may also be provided on the console 110 so it can be easily positioned as desired.

Figure 11:
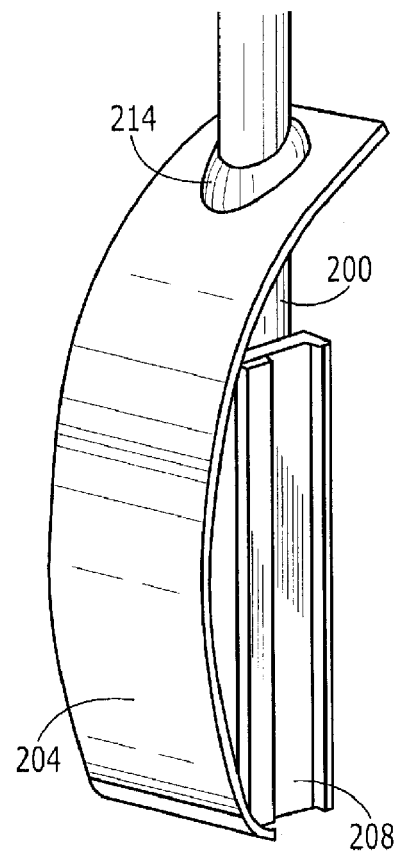
FIG. 11 is a detail view of the pole mount fixture shown in FIG. 10.
Figure 12:
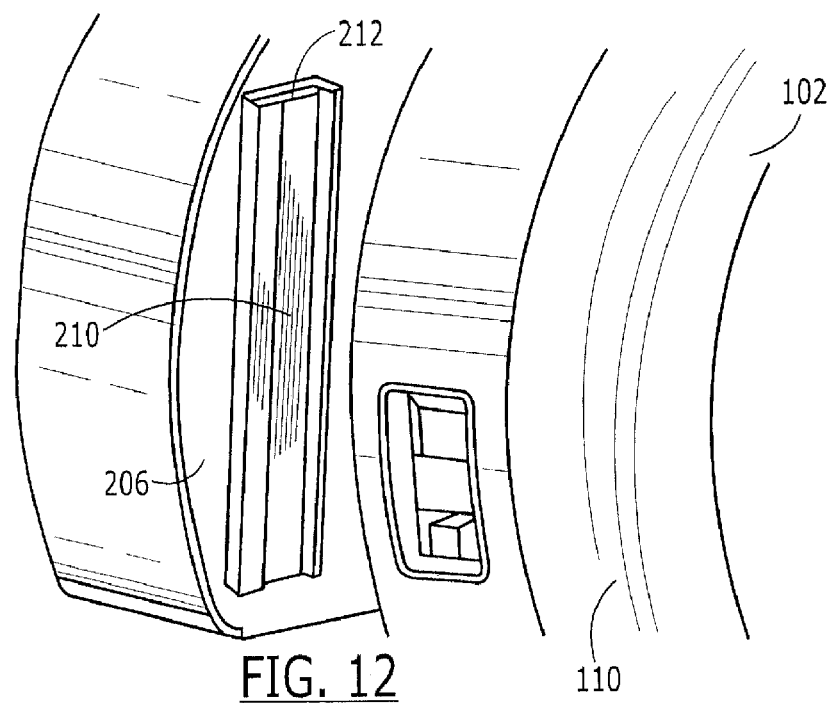
FIG. 12 is a detail view of the mating sliding mount fixture shown in FIG. 10.

FIGS. 10, 11 and 12 show an exemplary embodiment of a versatile mounting system according to the invention. According to the embodiment, a pole mounting fixture 204 separate from the console 110 is provided for coupling to a standard IV fluid pole 200. The console 110 includes a mating slide fitting 206 adapted to receive the pole mounting fixture 204 with a channel 208, or other guiding and retaining element, formed on the pole mounting fixture 204, to engage a corresponding guide element of the console 110, such as a protrusion or rail 210. A locking mechanism releasably attaching the pole mounting fixture 204 to the console 110 includes, for example, a latch 212 to retain the console 110 in a desired position on the pole 200. Alternatively, frictional contact between the pole mounting fixture 204 and the console 110 may be sufficient to retain them in a constant relative position, until detached by the user.

In the exemplary embodiment shown, the standard IV pole 200 is inserted through a passage 214 of the pole mounting fixture 204. As would be understood by those skilled in the art, the ease of sliding the pole 200 within the passage 214 may be controlled by selecting an amount of frictional contact between the pole 200 and the passage 214, or by providing an adjustable retaining device such as a screw or other conventional for pressing against or otherwise fastening to the pole 200. In a typical method of use, the pole mounting fixture 204 is attached to the pole 200, and then the console 110 is slid down over the pole attaching fixture 204 so that the channel 208, 210 mate. This configuration allows the console 110 to be mounted at a desired height selected by the user. In other embodiments, any of various clamping systems may be used to achieve the same objective. For example, a threaded screw clamp or a clamshell clamp may be used to connect the hydro-thermal ablation system 100 to the pole 200 as would be understood by those skilled in the art.

Figure 2:
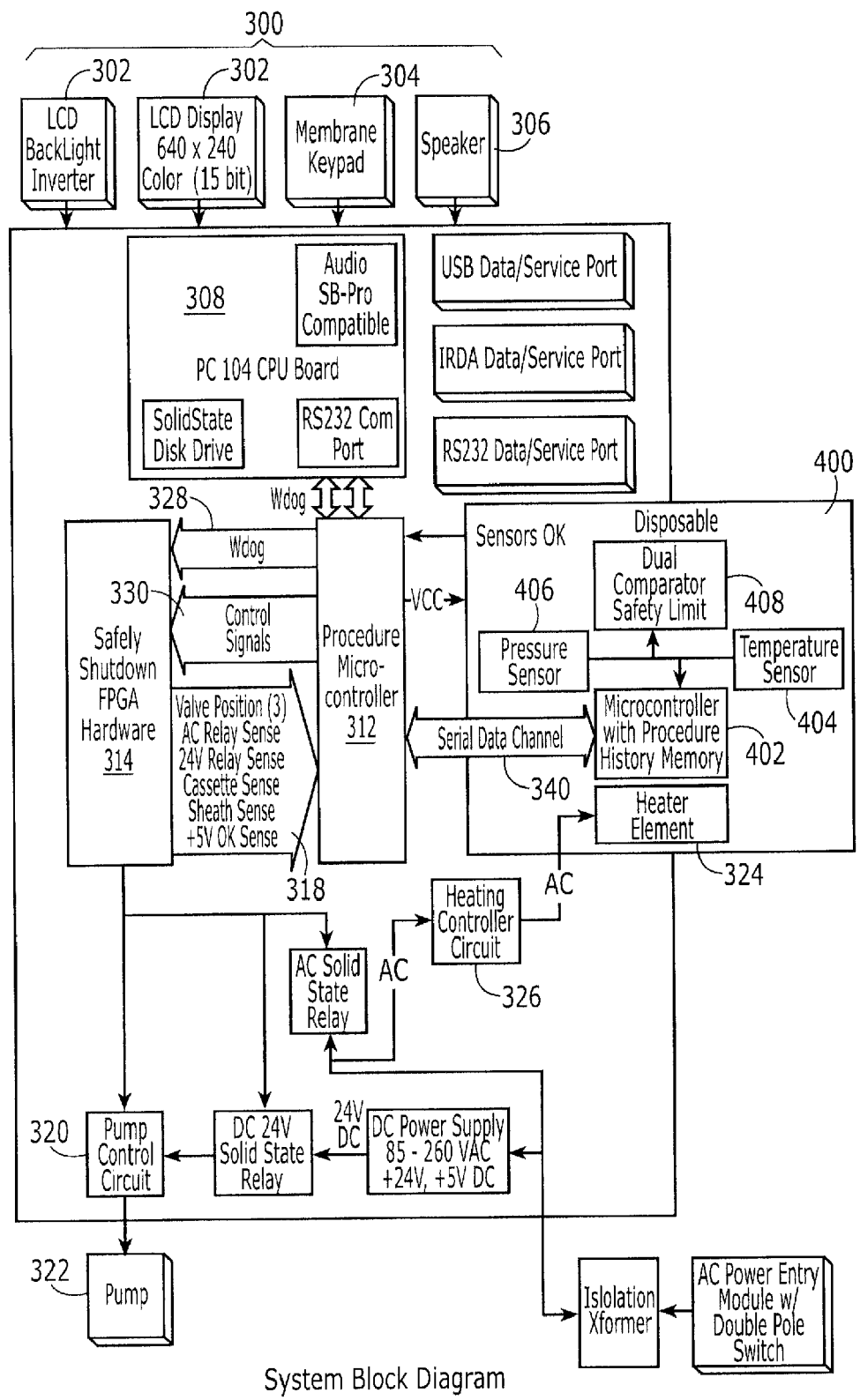
FIG. 2 is a block diagram showing an embodiment of an electrical system used in a device for circulating heated fluid to a patient, according to the invention.

The console 110 also contains one or more electronic processors and memory devices forming a control system of the hydro-thermal ablation system 100. FIG. 2 shows a block diagram of exemplary components of the hydro-thermal ablation system 100, as they are incorporated in the console 110. The controls of the hydro-thermal ablation system 100 include a user control system 300 to interface with the user and permit control and monitoring of procedures. A procedure controller 312 is also included, which comprises a firmware based control system controlling hydro-thermal ablation procedures performed by the system 100. For example, a memory unit may be used to store software which, when executed, instructs the electronic processors to carry out various functions. The procedure controller 312 also comprises an integral hardware based safety subsystem to ensure the safety of the patient at all times.

The exemplary user control system 300 shown in the figures comprises a display, for example LCD display 302, used to indicate the operational status of the system 100 and to provide help and guidance to the user. The display 302 may also define soft buttons and soft keys to supplement the keypad 304 as would be understood by those skilled in the art. A speaker 306 may also be used to provide additional status notification and prompts to the user. An embedded computer control board 308 runs core functions of the user control system 300. The controller board 308 may comprise, for example, a mass storage device storing instructions for the operation of the control board 308 and for storing system-use history information. The controller 308 may include a variety of interface hardware elements to connect to the LCD display 302, the keypad 304 and an audio output device such as a speaker 306. A data channel communicates with the procedures controller 312, for example to provide user control signals, and one or more additional data channels may be provided to perform system diagnostics tasks.

The procedure controller 312 is an independent control system dedicated to controlling all functions related to the hydro-thermal ablation procedure. The controller may function as an intelligent sequencer for tasks and actions of the system 100, such that the hydro-thermal ablation procedure is initiated upon receipt of a command from the user control system 300 via, for example, a serial data channel. Once a procedure has been initiated, the controller 312 begins the operational sequence for the selected procedure moving from one operational state to a next one based on the input received from the sensors connected to the controller 312, and on feedback signals received. The procedure controller 312 also generates various output signals, as desired during a particular state of the operation.

While a procedure is being carried out, the procedure controller 312 monitors a number of input lines 318 providing sensing and feedback functions. For example, the input lines 318 may comprise information on valve positions (for example relating to the three valves of the system), AC heater relay sensing, DC relay sensing (for pump and compressor supply), cartridge 112 in place sensing, sheath in place sensing, a +5 Volt "sensor status OK" signal, a "disposable sensors OK" signal and a watchdog input signal from the user control system 300. These several inputs are processed by the procedure controller 312 to determine the status of the devices of the system 100 and the progress of the hydro-thermal ablation procedure.

The procedure controller 312 is designed to control several components of the hydro-thermal ablation system 100. For example, the operation of the pump 322 may be controlled by procedure controller software via the pump control circuit 320. The operation of the heater 324, within the disposable procedure set 400, may also be controlled by the software via the heating controller circuit 326. A valve position control signal 330 may be generated by the procedure controller 312, and a watchdog output 330 (wdog) may be directed to the safety subsystems, to prevent damage to the equipment and injury to the patient. A hardware based safety subsystem 314 may also be used to monitor the input sensor lines, and may be programmed to prevent operation of the output devices when a failure condition is sensed.

In addition to the data communication taking place between the procedure controller 312 and the user control system 300, separate data channels may also be provided for other tasks. For example, a data channel 340 may be provided to permit the procedure controller 312 to communicate with the disposable procedure set 400 located in the disposable cartridge 112, to carry out monitoring and control functions of the disposable components of the hydro-thermal ablation system 100. A diagnostic data channel may also be provided, so that diagnostics and testing of the procedure controller 312 and of the other associated components can be performed easily by maintenance personnel.

The disposable data interface utilizing the data channel 340 is used to monitor various parameters of the disposable procedure set 400. For example, it may monitor the temperature and pressure of the heated saline fluid within the disposable cartridge 112, to monitor the status of the procedure as will be described in greater detail below. The interface may also be used to permanently record whether a disposable procedure set 400 has been used to carry out a procedure, so that the same disposable hardware cannot be reused. At the same time, the hardware safety subsystem 314 is used to also monitor "pressure ok" and "temperature ok" signals generated by the disposable procedure set 400, to provide a redundant fail safe operation in case of a leak or other problem during the procedure.

A diagnostic data interface may also be provided to the procedure controller 312. For example, a serial data channel may allow a service technician to establish a direct connection to the electronic board for the purpose of executing test and verification functions. Some or all of the test and verification functions may also be accessible via a diagnostic interface connector located on the user control system 300. Repair and upgrade of the procedure controller 312 is simplified and facilitated by providing redundant ways to test the electronic components of the hydro-thermal ablation system 100.

The display and user interface components of the hydro-thermal ablation system 100 are provided by the user control system 300. A color display, such as an LCD display 302 may be used to display a graphical user interface (GUI) with detailed instructional graphics and/or animations. As would be understood by those skilled in the art, commands may be actuated using a variety of soft keys and conventional hardware keys, such as membrane switches, that are well suited for use in a surgical environment. In one exemplary embodiment, a conventional operating system such as Microsoft's Windows CE™ is used in the electronic processor(s) of the console 110. Different screens are shown by the GUI for various phases of the surgical procedure to display pertinent data to the user. These screens may include a Set-Up Screen, a Diagnostic Hysteroscopy Screen, a Treatment Screen and a Fluid Loss Screen.

Another function of the console 110 is to control the pumping of heated fluid through the device. Since portions of the hydro-thermal ablation system 100 are disposable, it is important to retain as much hardware as possible in the non-disposable components, to minimize the cost of each procedure. However, many elements of the device contact fluids sent to the patient, and thus cannot be reused without complex sterilization procedures. In particular, the pumping of saline into and out of the patient presents challenges in reducing the hardware discarded after each use.

Figure 13:
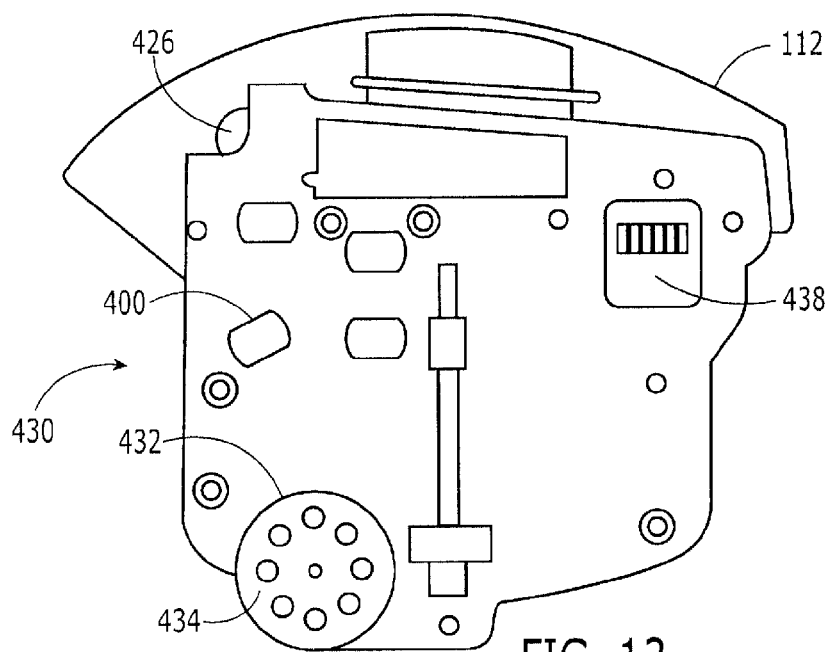
FIG. 13 is a representation showing a mating surface of a pumping cassette according to an embodiment of the invention.
Figure 14:
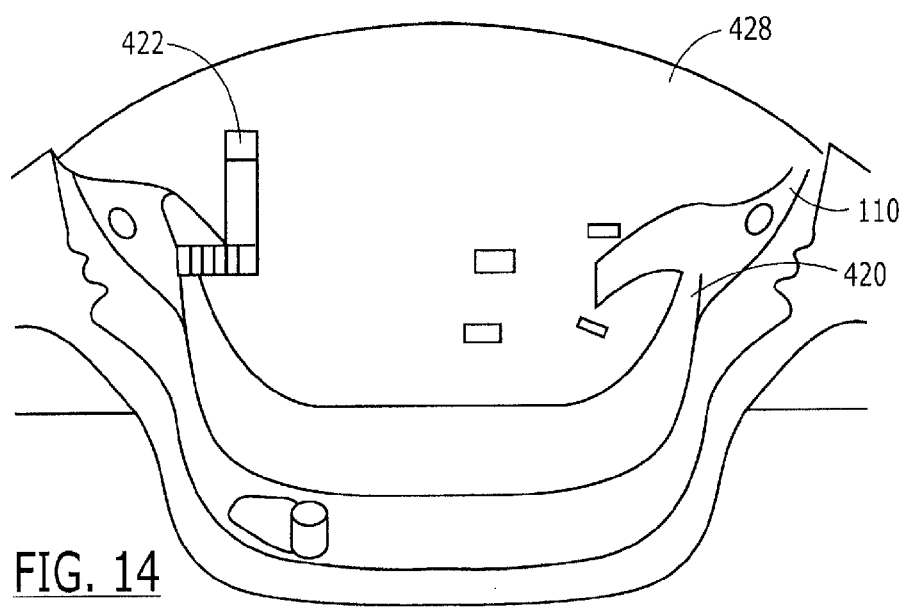
FIG. 14 is a representation showing a face of the console for receiving the pumping cassette shown in FIG. 13.
Figure 15:
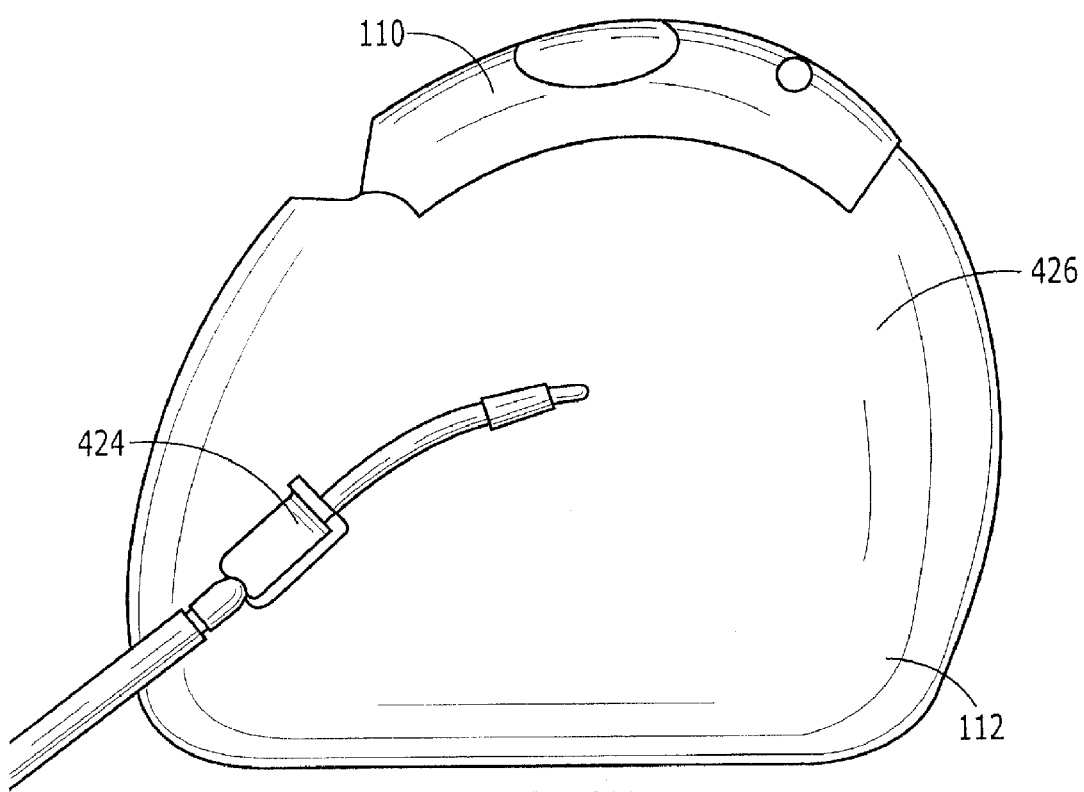
FIG. 15 is a representation showing the pumping cassette shown in FIG. 13 as installed in the console according to the invention.

In the present exemplary embodiment, saline is pumped by an impeller pump for which the motor is located in the reusable part of the device (e.g., in the console 110) with the impeller in the disposable cartridge (e.g., in the cartridge 112) shown in FIG. 1. All the pathways containing liquids pumped to or from the patient pass only through the disposable components, which are sterile before use, eliminating the possibility that those liquids will contaminate or be contaminated by the reusable components. The impeller is physically isolated from the motor to which it is magnetically coupled to rotationally drive the pump. Consequently, the motor is isolated from all of the fluids passing through the pump. There is thus no need to sterilize the motor or other reusable components of the device. FIGS. 13, 14 and 15 show an exemplary embodiment of a saline pumping mechanism of an hydro-thermal ablation device, that magnetically couples the motor to the impeller according to the present invention.

A mating surface 430 of the disposable cartridge 112 is shown in FIG. 13 and FIG. 14 shows a corresponding mating surface 420 of the console 110. These mating surfaces 420, 430 are aligned and brought into contact with one another when the cartridge 112 is attached to the console 110. For example, mechanical means such as latches may be used to releasably attach the two components to one another. Once the procedure has been completed, the cartridge 112 may be detached from the console 110 and disposed of. The disposable cartridge 112 is designed to fit on the console 110 in only one orientation, to maintain the correct relationship between the components. Monitoring of the disposable cartridge 112 is carried out with signals from sensors passing, for example, through electrical connectors 438 of the cartridge 112 that contact corresponding connectors 422 of the console 110.

In the exemplary embodiment, the impeller 432 housed inside the disposable cartridge 112 may be made inexpensively from plastic, for example by injection molding. Small and inexpensive magnets 434 attached to the impeller 432 may be included in the cartridge 112, to magnetically couple the impeller 432 to a motor located in the console 110. Any tubing necessary to bring fluid to and from the impeller 432 is attached to inlet and outlet ports of the housing within which the impeller 432 is mounted. For example, conduits 424 and 426 provide the flow to and from the impeller 432.

As indicated above, the disposable cartridge 112 and the console 110 fit together in only one orientation in which the magnets 434 of the impeller 432 are magnetically coupled to corresponding magnets of the motor. With this arrangement, the spinning of the motor rotates the impeller 432 propelling fluid through the system. The rotational speed of the impeller 432 may be controlled, for example, by varying a speed of the motor and/or the strength of the magnetic coupling.

The exemplary pump and impeller combination provides manufacturing advantages as there is no need to manufacture either element to high tolerances. The magnetic coupling increases the mechanical tolerance with respect to the location of the impeller 432 relative to the location of the motor. The impeller 432 is self-centering to a great extent with respect to a shaft axis of the motor, due to the centering properties of the magnetic coupling. In addition, the distance between the two sets of magnets also does not have to be maintained with a great degree of accuracy, since the magnetic coupling between the impeller 432 and the motor can take place over a significant range of distances. In the case of the impeller 432, ease of manufacture is especially important, since the component is disposable and thus should be inexpensive to manufacture.

In a different embodiment of the pumping system according to the invention, a more conventional peristaltic positive displacement pump may be used to move the heated saline solution. Here, multiple driver roller heads are used to drive flow through flexible tubing. In this embodiment, the pump motor and rollers are located in the console 110, and the flexible tubing is located in the disposable cartridge 112. This pumping system, however, requires loading the flexible tubing in a tortuous pathway before being used. This is time consuming and can be frustrating for the user if the tubing has to be loaded multiple times. Due to the repetitive squeezing and releasing of the rollers, the tubing may become cracked and may develop leaks. If the tubing is loaded incorrectly, it may be pinched by the rollers blocking flow and creating a back-pressure in the system.

Figure 3:
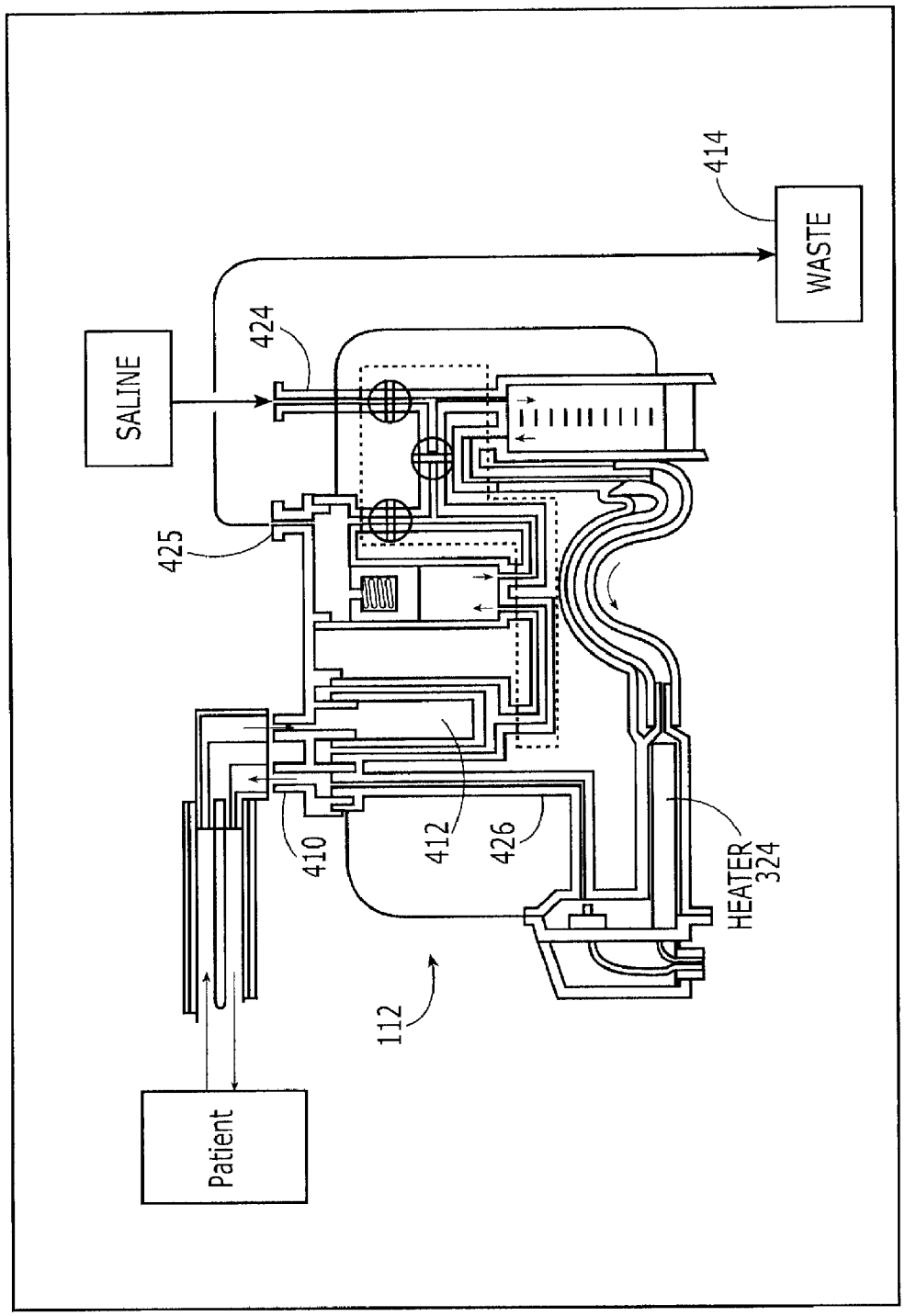
FIG. 3 is a diagram showing an embodiment of a tubing system used in a device for circulating heated fluid to a patient, according to the invention.

A second component of the hydro-thermal ablation system according to the invention is the disposable procedure set 400. One important element of the disposable procedure set is the cartridge 112 that interfaces with the reusable console 110 to provide heated and pressurized fluid for the procedure. As shown in FIGS. 2 and 3, an exemplary embodiment of the cartridge 112 according to the invention contains a heater element 324, pressure and temperature sensors 404 and 406, a safety monitor circuit 408 and an interface 410 to a sheath for the tubing set leading to the patient. When the disposable cartridge 112 is installed, it engages with contacts on the console 110 that provide electric power for the heater element 324, as well as with contacts that allow connection of the communications and safety monitoring signals with the procedure controller 312. For example, the electrical connectors 438, 422 may be used to provide power and data transmission to and from the cartridge 112.

The cartridge 112 may also be provided with an electronic processor to carry out certain functions independently from the CPU 308 of the reusable console 110. For example, a micro-controller 402 may be used to collect data from the pressure and temperature sensors 404, 406 that are also located within the cartridge 112. A communication pathway 340 may be provided to permit the micro-controller 402 to communicate with the CPU 308. A safety circuit 408 may be included in the design of the cartridge 112, to monitor the signals of the sensors 404, 406 and to ensure that they fall within specified limits. For example, the safety circuit 408 may generate a separate hardware "Sensor OK" signal when the sensors are within normal operating limits. If those limits are exceeded, the "Sensor OK" signal may be interrupted, triggering a signal indicating that an error condition has occurred. To prevent injuries and/or damage to the equipment, the safety hardware 314 and/or the CPU 308 of the console 110 may be adapted to execute a procedure that suspends the ablation procedure when the "Sensor OK" signal is not received.

The micro-controller 402 may also be designed to record the sensor data in a non volatile memory. As described above, this feature may be used to ensure that a disposable procedure set 400 is never reused and to assure a user that the currently connected disposable procedure set 400 has never been used before. For example, the processor 308 of the console 110 may read the data stored by the micro-controller 402, and prevent operation of the system 100 if the memory is not clear (i.e., indicating prior use of the cartridge 112). If there is no data stored in the memory when the cartridge 112 is first connected, the console 110 determines that the disposable procedure set 400 has never been used and that the procedure can be carried out.

A procedure according to one embodiment of the present invention utilizes heated saline solution as an ablation fluid. As described above, the mechanism for heating the fluid is located within the cartridge 112, and is part of the disposable procedure set 400. In one exemplary embodiment, the saline is heated by an integrated temperature controller powering a cartridge heater. The heater is located within the cartridge 112, as shown in FIGS. 2 and 3. Temperature control of the saline may be carried out using, for example, thermistors incorporated into the cartridge 112. As described above, all portions of the heating device 324 which contact fluids that flow to and from the patient are disposed of after the procedure has been completed. As the reusable portions of the heating device do not contact these fluids, there is no need to sterilize any part of the heating device.

A filter 412 may also be located within the cartridge 112, as shown in FIG. 3. For example, the filter 412 may be a macro-particulate trap located in the disposable portion of the hydro-thermal ablation system 100, to filter the saline or other fluid used in the ablation procedure. As would be understood by those skilled in the art, a filter bypass may be built in together with the filter 412, to prevent damage to the device if clogging causes a flow restriction through the filter 412. In addition, the direction followed by the fluid in the flow path during different phases of the procedure is controlled by valves (e.g., pinch valves) located in the console 110, and acting on flexible portions of the flow path located in the disposable cartridge 112. These valves are activated by an opening/closing mechanism which may, for example, include solenoids actuating pinch valves under control of the CPU 308 of the console 110.

Air and excess fluid are drained into a waste container 414 via a venting port 425. The waste container 414 may comprise a flexible container (such as a bag formed by a thin film), a semi-rigid container or a rigid container. In one exemplary embodiment, the waste container 414 includes fluid volume graduations that can be read on the outside of the container, to facilitate post-procedure fluid balance analyses.

Figure 17:
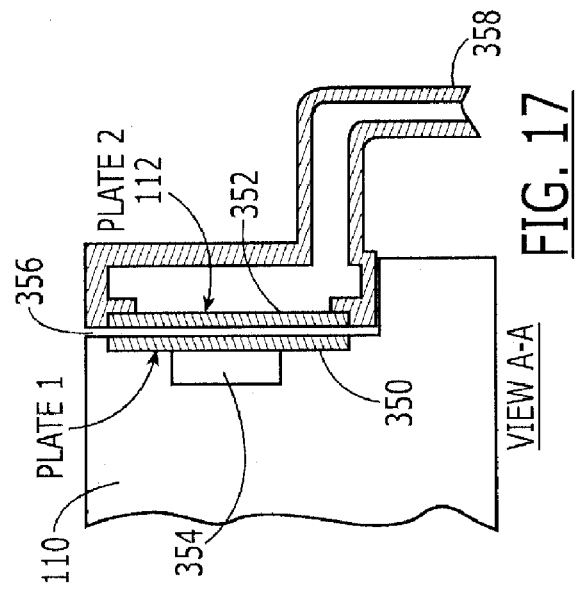
FIG. 17 is a detail diagram showing a view along line A-A of the temperature transfer apparatus shown in FIG. 16.
Figure 16:
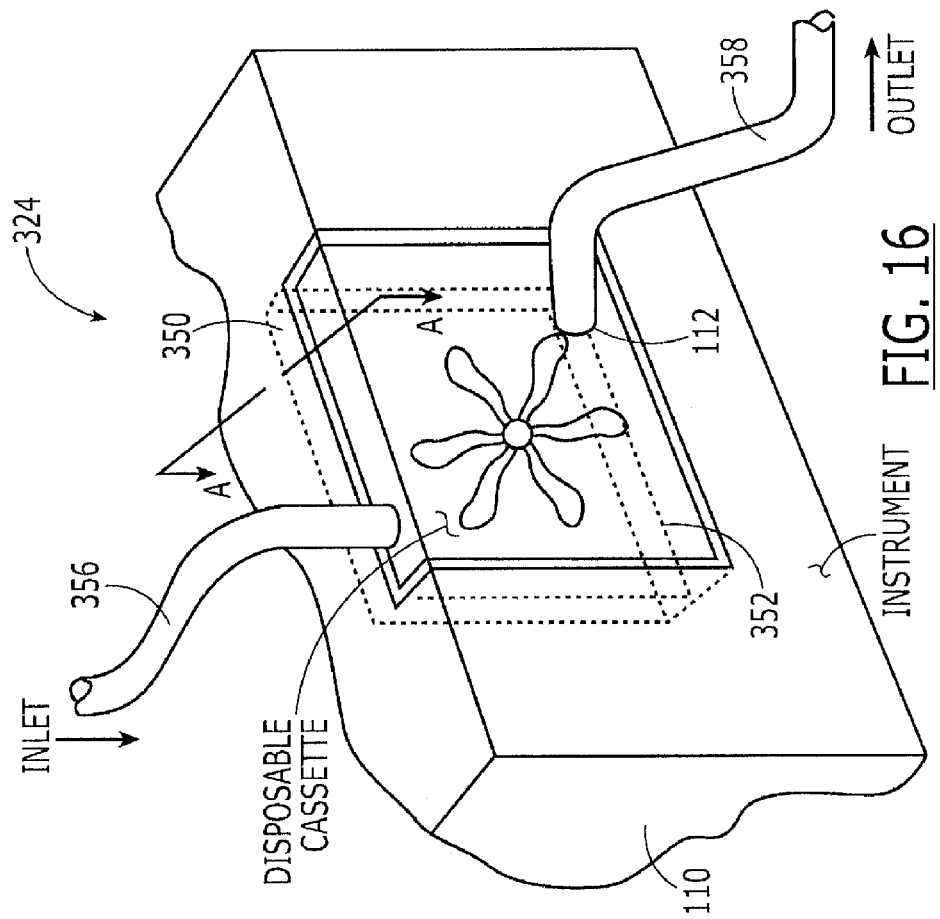
FIG. 16 is a diagram showing a temperature transfer apparatus according to an embodiment of the present invention.

A more detailed view of the heating device 324 and its associated elements is shown in FIGS. 16 and 17. In this exemplary embodiment of the heating device 324, the temperature of the fluid is controlled by conduction of heat from a first plate to a second plate. The reusable first plate 350 which resides in a reusable portion of the device, for example the console 110, is actively heated by, for example, a heating element 354 controlled by the microprocessor 308. As with the other reusable parts of the system 100, the plate 350 never contacts fluids routed to the patient and does not require sterilization for reuse. A disposable second plate 352, located within the cartridge 112, passes heat to fluid passing through the cartridge 112 and flowing along the disposable second plate 352 to receive heat therefrom. When the cartridge 112 is engaged with the console 110, the plates 350, 352 are in intimate contact, so that heat passes from the heated reusable plate 350 to the disposable plate 352 which then heats the fluids passing to the patient.

According to the present exemplary embodiment, fluid enters the heating device 324 within the cartridge 112 via an inlet tube and, after being heated, exists the heating device 324 via an outlet tube 358. Additional fluid passages within the cartridge 112 route the heated fluid to other components of the disposable procedure set 400, so that it can be directed to target tissue within the patient. As with the other elements of the system 100, the exemplary arrangement of the heating device 324 allows the more expensive elements (e.g., heating element 354 and the associated temperature regulating processors) to be placed in the reusable console 110. The cost of the disposable components of the hydro-thermal ablation device is therefore reducing the overall cost of the hydro-thermal ablation procedure.

According to the invention, the flow path through the disposable cartridge 112 engages the active components of the system 100, such as heaters and pumps housed in the reusable console 110, without bring any contaminating fluids into contact with those active components. In one exemplary embodiment, the disposable plate 352 makes up a large portion of the side of the cartridge 112 that contacts the console 110, to maximize the heat exchange surface available. As would be understood by those skilled in the art, one or both of the plates 350, 352 may be made of a piece of metal, such as stainless steel, or of a heat conducting polymer. The plates may also be made of a metal encapsulated in plastic to, for example, prevent direct contact between the metal and the fluid.

Figure 4:
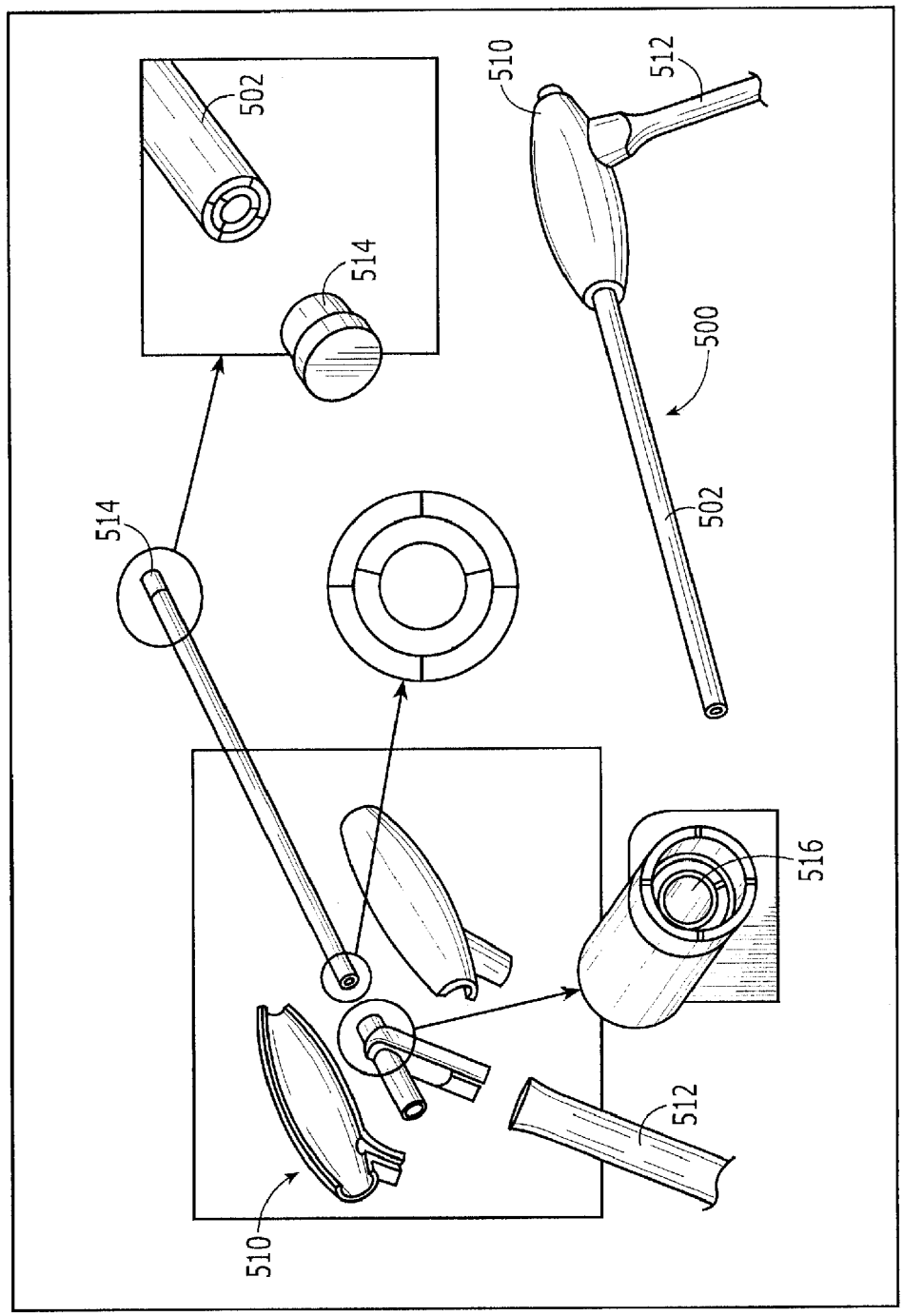
FIG. 4 is an assembly drawing showing a patient sheath according to an embodiment of the present invention.
Figure 5:
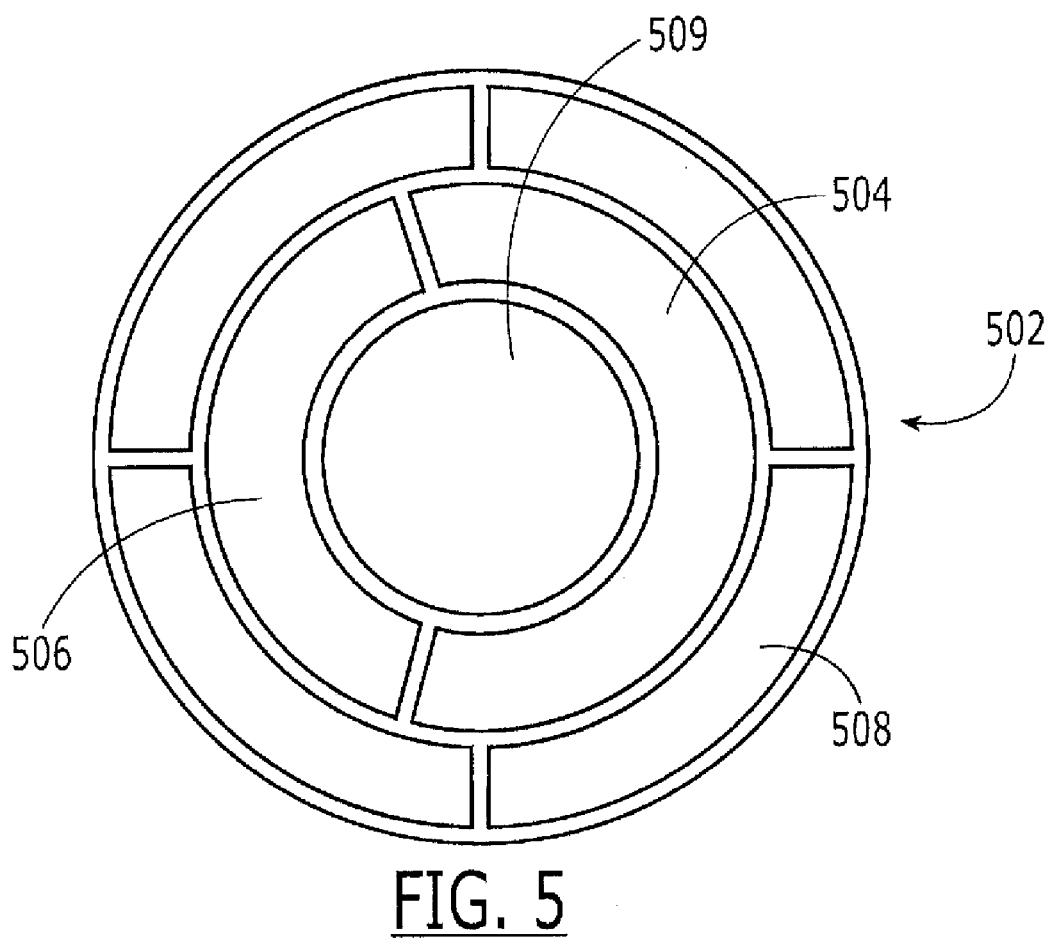
FIG. 5 is a cross sectional view showing a detail of the sheath tubing according to the invention.

Another component of the disposable procedure set 400 is a patient sheath 500 as shown in FIGS. 4, 5 and 6 which delivers heated saline from the disposable cartridge 112 to the uterus. The sheath 500 is inserted into the uterus via the cervical canal with an outer diameter of an insertion portion 502 of the sheath 500 forming a fluid tight seal with the wall of the cervical canal to prevent leakage of the heated saline through the cervix into the vaginal canal. The insertion portion 502 preferably has an outer diameter appropriate to the anatomy of the patient. For example, the outer diameter of the insertion portion 502 may preferably be between about 6 mm and about 8 mm.

The sheath 500 may further include one or more additional features to aid in the establishment and maintenance of a fluid tight seal within the cervical canal. This may be especially useful in cases where the patient has unusual anatomical features such as a tapering of the cervical canal, a very oval or out of round cervical canal, a short cervical canal and/or tearing or scarring caused by prior events or surgical procedures. The sealing features that may be used with the insertion portion 502 of the sheath 500 include inflatable balloons, suction devices, mechanical stoppers, and sponges/foams/other absorbent devices as would be understood by those skilled in the art. Additionally, features may be incorporated at a tip 514 of the insertion portion 502 to prevent burns to the patient. For example, features allowing active fluid irrigation of adjacent tissues or active cooling of the sheath 500 may be included.

FIG. 4 shows an exploded view of the patient sheath 500 including an ergonomic handle 510 which may, for example, be formed of multiple joined parts to provide a comfortable grip to the surgeon. The handle 510 may also comprise a tenaculum stabilizer 522, shown in FIG. 6, for establishing a connection between the sheath 500 and a cervical tenaculum used to grasp the cervix. The tenaculum stabilizer 522 allows the user to conveniently hold the sheath 500 and the tenaculum with a single hand, and prevents the sheath 500 from inadvertently being removed during the procedure.

As shown in FIG. 4, the sheath 500 may be formed of multiple parts. The insertion portion 502 according to this embodiment is attached to a connector 516 of the handle 510 that operatively connects the insertion portion 502 to the conduit 512 which is preferably fluidly connected to the outlet 358 of the heater unit 324 as shown in FIG. 16. The insertion portion 502 preferably comprises multiple passages serving different functions For example, as shown in FIG. 5, an inner lumen 509 allows passage for an endoscope or hysteroscope enabling visualization of the target tissue while passages 504 and 506 convey heated saline to and from the patient, respectively, to recirculate fluids. Outer passages 508 may serve as insulation to prevent the heat from the fluid flowing therethrough from damaging non-targeted tissue. Furthermore, FIG. 7 shows a patient sheath 500' substantially similar to the sheath 500 except that a camera head and scope 520 are connected thereto.

The inner lumen 509 of the sheath 500 is preferably designed to accommodate a range of rigid hysteroscopes including, for example, scopes of approximately 3 mm in diameter. Disposable scope adapters may also be provided as part of the disposable procedure set 400, allowing the user to select an appropriate adapter for a scope of choice. In another embodiment according to the invention, the sheath 500 incorporates a fiber-optic element of, for example, 2 mm diameter extending the length of the device. An optical system using the fiberoptic element is preferably compatible with standard camera heads and is sized to be located within the inner lumen 509. Using such a disposable fiber-optic element eliminates the time and complexity associated with preparing and inserting a hysteroscope.

System priming of the patient sheath 500 can be facilitated in a non-sterile field by using a bypass 600 disposed at the end of the conduit 512 that can be covered by a film. As shown in FIGS. 8 and 9, the openings of the two lumens of the conduit 512 are covered by films 604, 606 which are preferably permeable to a gas (for example Ethylene Oxide used for sterilization) but not to liquids. In this manner the system may be primed outside of a sterile field, for example by a circulating nurse, while the patient sheath 500 remains in the sterile field. When the user is ready to commence the procedure, the films 604, 606 are punctured, for example, using sharp ends 610 that extend from the handle 510 and that connect to fluid passages within the insertion portion 502. A lock with push button release 602 may be used to connect the two components during use. According to the invention, the optics and sheath 500 can be prepared for use by the physician when ready, and may be connected to the conduit 512 at the last minute, just before starting the procedure.

An important aspect of the exemplary hydro-thermal ablation system 100 is the monitoring and control of fluid pressure and fluid loss within the system Elements of the reusable console 110 and of the disposable cartridge 112 cooperate to ensure that the pressure of fluid is maintained at a level consistent with correct operation of the system 100 to prevent damage to the device and injury to the patient. In the exemplary embodiments described above, the CPU board 308, the procedure micro-controller 312 and the safety hardware 314 of the console 110 form a part of the protective and safety system of the device. Another part is comprised of the micro-controller 402 and by the sensors 404, 406 of the cartridge 112.

Pressure in the system is established and maintained by a pump and by a motorized control piston that communicates with a pressure sensor. A pressure sensor, sensor 406 for example, is incorporated in the disposable cassette. The control piston is located in the reusable console 110 below a recess where the disposable cassette 112 is inserted into the console 110. Whenever a change in fluid pressure occurs as a result of system expansion or of a slow leak, the piston advances or retracts as necessary to move fluid into or out of a syringe-like chamber located in the disposable cassette 112 to return the system pressure to a desired level. Movement of the piston is shown by arrows drawn in the syringe-like chamber. The piston is located within the console 110 while the syringe-like chamber is in the cartridge 112. Therefore, a fluid tight mechanical connection between the two components is provided, to change the chamber's volume without letting fluid into the console 110.

According to embodiments of the invention, the piston adds or removes fluid from the system to maintain the desired fluid pressure. In one exemplary embodiment, the target system pressure is approximately 65 mmHg during a diagnostic phase of hysteroscopy procedure and approximately 50 mmHg during a treatment phase. In addition to the pressure controlled piston system, a mechanical pressure relief valve may also be provided for additional over pressure relief protection to the system. In the exemplary embodiment shown in FIG. 3, the mechanical pressure relief valve may be a spring-loaded valve that controls access to the waste/drainage bag.

The system 100 monitors movement of the pressure control piston to determine an amount of fluid loss. When a total amount of fluid loss or a rate of fluid loss exceeds a predetermined threshold value, a warning signal is generated by the hydro-thermal ablation system 100. In addition, the system 100 may also shut down when either or both of these threshold values is exceeded. As described above, the pressure control piston is preferably located in the console 110, while the pressure sensor 406 is located in the cartridge 112. Various set points may be used to indicate the condition of the system based on fluid loss. For example, a fluid loss of about 10 cc may be set to generate a "fluid loss alarm" triggering the console 110 to provide basic troubleshooting directions for the user. Critical information about the event, such as a fluid loss rate, fluid loss amount and a system pressure may also be displayed to the user on a screen. The GUI of the user control system 300 may be used to provide this information graphically.

The monitoring of the system pressure may also be used to whether dangerous conditions are about to occur or are already taking place. As would be understood by those of skill in the art, a change in pressure may be brought about by expansion of the system volume, which may result from tubing compliance or from expansion of human tissue or organs. Alternatively, a pressure change may be due to absorption of the ablation fluid into the tissue which may be harmful. For example, if the system replaces more than about 10 ml of fluid due to a loss of fluid volume, it may be inferred that fluid is being absorbed by the patient's body. In the exemplary embodiment, a detection of a 10 ml fluid loss may trigger an alarm. After, for example, three such alarms have been signaled, the system may enter a cooling and/or flushing cycle. The hydro-thermal ablation procedure may thus be suspended, or at least the addition of fluid may be inhibited to prevent injury to the patient.

The present invention has been described with reference to specific exemplary embodiments. Those skilled in the art will understand that changes may be made in details, particularly in matters of shape, size, material and arrangement of parts. Accordingly, various modifications and changes may be made to the embodiments described herein. The specifications and drawings are, therefore, to be regarded in an illustrative rather than a restrictive sense.

What is claimed is:

1. A system for ablating tissue, comprising:
    a reusable control unit including a processor monitoring and controlling ablation and a control interface receiving input to and output from the processor;
    a disposable procedure set releasably connectable to the control unit to couple to the control interface for communication with the processor; and
    a procedure controller adapted to monitor signals of sensors provided in the system to recognize absorption of fluid by the patient.

2. The system of claim 1, wherein the procedure set comprises a cartridge including a heat transfer unit and a pump.

3. The system of claim 2, wherein the cartridge is electrically coupled to the control unit when the procedure set is connected to the control unit.

4. The system of claim 2, wherein the procedure set further comprises a patient sheath releasably connectable to the cartridge.

5. The system of claim 4, wherein the patient sheath includes a sealing film covering openings to patient sheath lumens and wherein the sealing film is punctured to couple the sheath to the cartridge.

6. The system of claim 2, wherein the pump includes an impeller magnetically coupled to a motor in the control unit.

7. The system of claim 2, wherein the cartridge comprises sensors for monitoring pressure and temperature of the fluid, the sensors being electrically coupled to the processor via the control interface.

8. The system of claim 2, wherein the heat transfer unit transfers heat to an ablation fluid under control of the processor to bring the ablation fluid to a desired temperature and the pump applies pressure to the ablation fluid under control of the processor to maintain a pressure in the ablation fluid at a desired level.

9. The system of claim 8, wherein the control unit comprises a heating element coupled to the processor which, when the cartridge is connected to control unit, is adjacent to a heat transfer unit of the cartridge.

10. The system of claim 9, wherein the heating element comprises a plate actively heated by a heater within the control unit, wherein the plate is adjacent to the heat transfer element, a side of the heat transfer element adjacent to the plate being opposite a side of the heat transfer element which contacts the ablation fluid to isolate the heat transfer element from the ablation fluid.

11. The system of claim 8, wherein the processor comprises a hardware based safety subsystem monitoring input from the control interface and inhibits ablation based on input from the control interface indicating that the system is operating outside an acceptable range for a safety parameter.

12. The system of claim 11, wherein the safety parameter is a measured amount of fluid loss.

13. The system of claim 11, wherein the safety parameter is a fluid pressure level.

14. The system of claim 11, wherein the safety subsystem inhibits ablation by preventing operation of the pump to supply additional ablation fluid while the system is operating outside the acceptable range for the safety parameter.

15. The system of claim 14, wherein the safety subsystem inhibits ablation by preventing further heating of the ablation fluid while the system is operating outside the acceptable range for the safety parameter.

16. The system according to claim 15, wherein the processor inhibits ablation when a pressure of the ablation fluid is one of less than 45 mmHG and greater than 55 mmHG.

17. The system of claim 1, further comprising a user interface of the reusable control unit providing user commands to the processor and providing to the user feedback from the processor.

18. The system of claim 17, wherein the user interface further includes a memory module storing system use information and instructions executable by the user interface.

19. The system of claim 1, wherein the procedure controller is provided in the control unit.

20. A control system for a hydro-thermal ablation procedure, comprising:

a reusable console including a processor monitoring and controlling the hydro-thermal ablation procedure, wherein the processor is configured to recognize absorption of a fluid by the patient;
  a disposable cartridge selectively coupleable to the console, the cartridge including a plurality of sensors connectable to the processor, the sensors measuring properties of an ablation fluid;
  a mechanical safety interlock of the processor inhibiting the hydro-thermal ablation procedure when commanded by the processor; and
  an ablation fluid control system including a pump and a heater controlled by the processor.

21. The control system of claim 20, wherein the cartridge includes a plate a first side of which is configured to contact the ablation fluid wherein, when the cartridge is coupled to the console, a second side of the plate is adjacent to a heat transfer member of a heating element.

22. The control system of claim 20, wherein the pump comprises an impeller in the disposable cartridge and a motor in the reusable console.

23. The control system of claim 20, wherein a first one of the sensors monitors a pressure of the ablation fluid and wherein the processor stops the pump when the monitored fluid pressure indicates a leak.

24. The control system of claim 20, wherein the processor controls a plunger element to add and remove fluid volume to maintain a desired fluid pressure.

25. The control system of claim 20, wherein the processor monitors the addition of ablation fluid to recognize absorption of the fluid by the patient.

* * * * *